US010314825B2

(12) United States Patent
Nakamura et al.

(10) Patent No.: US 10,314,825 B2
(45) Date of Patent: Jun. 11, 2019

(54) AGENT FOR TREATMENT OF PBC

(71) Applicant: KOWA COMPANY, LTD., Nagoya-shi (JP)

(72) Inventors: Mitsumasa Nakamura, Chuo-ku (JP); Satoshi Kojima, Chuo-ku (JP); Ryohei Tanigawa, Chuo-ku (JP)

(73) Assignee: KOWA COMPANY, LTD., Nagoya-shi (JP)

( * ) Notice: Subject to any disclaimer, the term of this patent is extended or adjusted under 35 U.S.C. 154(b) by 0 days.

(21) Appl. No.: 15/903,279

(22) Filed: Feb. 23, 2018

(65) Prior Publication Data
US 2018/0250274 A1 Sep. 6, 2018

Related U.S. Application Data

(60) Provisional application No. 62/463,258, filed on Feb. 24, 2017.

(51) Int. Cl.
*A61K 31/423* (2006.01)
*A61P 1/16* (2006.01)
*A61K 31/575* (2006.01)

(52) U.S. Cl.
CPC .......... *A61K 31/423* (2013.01); *A61K 31/575* (2013.01); *A61P 1/16* (2018.01)

(58) Field of Classification Search
CPC .................................................. A61K 31/423
See application file for complete search history.

(56) References Cited

U.S. PATENT DOCUMENTS

2005/0101636 A1 5/2005 Yamazaki et al.
2006/0189667 A1 8/2006 Yamazaki et al.

FOREIGN PATENT DOCUMENTS

WO 2005/023777 A1 3/2005

OTHER PUBLICATIONS

Honda et al., Pemafibrate, a novel selective peroxisome proliferator-activated receptor alpha modulator, improves the pathogenesis in a rodent model of nonalcoholic steatohepatitis, Scientific Reports | 7:42477, Feb. 14, 2017.*
Doumen, Anti-hyperlipidemic agent in the treatment of liver diseases: prospect of fenofibrate (Lipanthyl®), Prog. Med., Jan. 2005, vol. 25, No. 1, pp. 103, 104, 107 and 108 (partial translation).*
Selmi et al.—"Primary biliary cirrhosis", *Lancet* May 7, 2011, vol. 377, pp. 1600-1609.
Carey et al.—"Primary biliary cirrhosis", *Lancet*, Oct. 17, 2015, vol. 386, pp. 1565-1575.
Silveira et al.—"American Association for the Study of Liver Diseases Endpoints Conference: Design and Endpoints for Clinical Trials in Primary Biliary Cirrhosis", *Hepatology*, Jul. 2010, vol. 52, No. 1, pp. 349-359.
Boonstra et al.—"Epidemiology of primary sclerosing cholangitis and primary biliary cirrhosis: A systematic review", *Journal of Hepatology*, 2012, vol. 56, No. 5, pp. 1181-1188.
Boonstra et al.—"Rising incidence and prevalence of primary biliary cirrhosis: a large population-based study", Liver International ISSN 1478-3223 (2014), 8 pages.
Lindor et al.—"Primary Biliary Cirrhosis", AASLD Practice Guidelines, Hepatology, Jul. 2009, pp. 291-308.
Huet et al.—"Impact of Fatigue on the Quality of Life of Patients with Primary Biliary Cirrhosis", The American Journal of Gastroenterology, vol. 95, No. 3, 2000, pp. 760-767.
Bergasa—"The pruritus of cholestasis", Journal of Hepatology, 43 (2005), pp. 1078-1088.
Pares et al.—"Excellent Long-Term Survival in Patients with Primary Biliary Cirrhosis and Biochemical Response to Ursodeoxycholic Acid", Gastroenterology, 2016, vol. 130, No. 3, pp. 715-720.
Nevens et al.—"A Placebo-Controlled Trial of Obeticholic Acid in Primary Biliary Cholangitis", The New England Journal of Medicine, 375:7, Aug. 18, 2016, pp. 631-643.
Iwasaki et al.—"Bezafibrate may have a beneficial effect in pre-cirrhotic primary biliary cirrhosis", Hepatology Research 16 (1999), pp. 12-18.
Hazzan et al.—"Bezafibrate Treatment of Primary Biliary Cirrhosis Following Incomplete Response to Ursodeoxycholic Acid". J Clin Gastroenterol, vol. 44. No. 5, May/Jun. 2010, pp. 371-373.
Kurihara et al.—"Investigation Into the Efficacy of Bezafibrate Against Primary Biliary Cirrhosis, With Histological References From Cases Receiving Long Term Monotherapy", Am J Gastroenterol, vol. 97, No. 1, 2002, pp. 212-214.
Kurihara et al.—"Bezafibrate in the Treatment of Primary Biliary Cirrhosis: Comparison with Ursodeoxycholic Acid" Am J Gastroenterol, vol. 95, No. 10, 2000, pp. 2990-2992.
Nakai et al.—"Combination Therapy of Bezafibrate and Ursodeoxycholic Acid in Primary Biliary Cirrhosis: A Preliminary Study", Am J Gastroenterol, Jan. 2000, 95, pp. 326-327.
Ohmoto et al.—"Effect of bezafibrate in primary biliary cirrhosis: a pilot study", Liver 2001, 21, pp. 223-224.
Takeuchi et al.—"Additive improvement induced by bezafibrate in patients with primary biliary cirrhosis showing refractory response to ursodeoxycholic acid", Journal of Gastroenterology and Hepatology 26 (2011), pp. 1395-1401.
Dohmen et al.—"Fenofibrate for patients with asymptomatic primary biliary cirrhosis", World J Gastroenterol 2004, vol. 10, No. 6, pp. 894-898.
Han et al.—"Efficacy of fenofibrate in Chinese patients with primary biliary cirrhosis partially responding to ursodeoxycholic acid therapy", Journal of Digestive Diseases 2012, 13, pp. 219-224.
Levy et al.—"Pilot study: fenofibrate for patients with primary biliary cirrhosis and an incomplete response to ursodeoxycholic acid", Aliment Pharmacol Ther 2011, 33, pp. 235-242.
Liberopoulos et al.—"Fenofibrate in Primary Biliary Cirrhosis: A Pilot Study", The Open Cardiovascular Medicine Journal 2010. 4, pp. 120-126.

(Continued)

*Primary Examiner* — Svetlana M Ivanova
(74) *Attorney, Agent, or Firm* — Oblon, McClelland, Maier & Neustadt, L.L.P.

(57) ABSTRACT

The present invention relates to a pharmaceutical composition for the treatment of primary biliary cirrhosis (PBC), in which containing a therapeutically effective amount of (R)-2-[3-[[N-(benzoxazol-2-yl)-N-3-(4-methoxyphenoxy)propyl]aminomethyl]phenoxy] butyric acid, a salt thereof, or a solvate thereof.

5 Claims, 4 Drawing Sheets

(56) References Cited

OTHER PUBLICATIONS

Ohira et al.—"Fenofibrate Treatment in Patients With Primary Biliary Cirrhosis". AJG vol. 97, No. 8, 2002, pp. 2147-2149.

Hosonuma et al.—"A Prospective Randomized Controlled Study of Long-Term Combination Therapy Using Ursodeoxycholic Acid and Bezafibrate in Patients With Primary Biliary Cirrhosis and Dyslipidemia". The American Journal of Gastroenterology, Mar. 2015, vol. 110, pp. 423-431.

Lammers et al.—"Levels of Alkaline Phosphatase and Bilirubin Are Surrogate End Points of Outcomes of Patients With Primary Biliary Cirrhosis: An International Follow-up Study", Gastroenterology Dec. 2014, 147, pp. 1338-1349.

Cheung et al.—"Time to make the change from 'primary biliary cirrhosis' to 'primary biliary cholangitis'", Can J Gastroenterol Hepatol vol. 29, No. 6, Aug./Sep. 2015.

European Association for the Study of the Liver—"EASL Clinical Practice Guidelines: Management of cholestatic liver diseases", Journal of Hepatology 51 (2009), pp. 237-267.

Ikejima, K., Advance of Treatment of Liver, Gallbladder and Pancreas (recent 30 years), Kan Tan Sui, Dec. 2010, vol. 61 No. 6, pp. 1107 to 1111 (with partial English translation).

Dohmen, K., et al., "The Effectiveness of Fenofibrate in Comparison to Bezafibrate for Patients with Asymptomatic Primary Biliary Cirrhosis", Fukuoka Acta Med., 2013, vol. 104 No. 10, pp. 350-361 (with English translation).

Iwasaki, S., et al., "Mechanism of Treatment of Bile Stasis in Primary Biliary Cirrhosis—Combination therapy of UDCA and bezafibrate", Kan Tan Sui, May 2016, vol. 72 No. 5, pp. 869 to 876 (with partial English translation).

Doumen, K., "Anit-hyperlipidemic Agent in the Treatment of Liver Diseases: Prospect of Fenofibrate (Lipanthyl®)", Prog. Med., Jan. 2005, vol. 25 No. 1, pp. 103 to 109 (with partial English translation).

Merck Manual 18th Edition Japanese language Edition, First Edition, 3rd Print, Nikkei Business Publications, Inc., Apr. 25, 2007, pp. 229 to 231 (with English translation).

Ishibashi, S., et al., "Effects of K-877, a Novel Selective PPARα Modulator (SPPARMα), in Dyslipidaemic Patients; A Randomized, Double Blind, Active- and Placebo-Controlled, Phase 2 Trial", Atherosclerosis, vol. 249, 2016, pp. 36-43 (with cover pages).

\* cited by examiner

AGENT FOR TREATMENT OF PBC

BACKGROUND

Technical Field

The present invention relates to treatment of primary biliary cirrhosis (PBC).

Related Art

Primary biliary cirrhosis (PBC) is chronic progressive cholestatic liver disease, resulting in destruction and fibrosis of liver parenchymal cells along with chronic cholestasis. As the symptoms progresses, finally it may lead to a serious outcome such as liver cirrhosis, or liver failure (Selmi C, et al.; Lancet. 2011; 377 (9777): 1600-1609, Carey E J, et al.; Lancet. 2015; 386 (10003): 1565-1575, and Silveira M G, et al.; Hepatology. 2010; 52 (1): 349-359). PBC is a rare disease willingly developed in women (prevalence is around 1 to 40 people per 100,000 people), and the morbidity is on an increasing trend year by year (Boonstra K, et al.; Journal of Hepatology. 2012; 56 (5): 1181-1188, and Boonstra K, et al.; Liver International. 2014; 34: e31-e38). In addition, currently, discussion to change the disease name to "primary biliary cholangitis (PBC)" is under way (Angela C Cheung, et al.; Can J Gastroenterol Hepatol Vol. 29 No. 6 August/September 2015; 293).

It is considered that pathogenesis of PBC is due to an autoimmune mechanism, and in approximately 95% of patients with PBC, an anti-mitochondrial antibody (AMA) that is an autoantibody is detected (Lindor K D, et al.; Hepatology. 2009; 50: 291-308). Further, as a characteristic of major biochemical laboratory findings of patients with PBC, a high level of alkaline phosphatase (ALP) can be mentioned (Lindor K D, et al.; Hepatology. 2009; 50: 291-308). In many of patients with PBC, clinical symptoms are not observed, and the diagnosis of PBC is performed on the basis of abnormalities of laboratory data such as AMA positive, and high level of ALP. Typical clinical symptoms of patients with PBC are fatigue and itching, and these symptoms significantly impair the quality of life (QOL) of patients with PBC (Selmi C, et al.; Lancet. 2011; 377 (9777): 1600-1609, Carey E J, et al.; Lancet. 2015; 386 (10003): 1565-1575, Huet P M, et al.; Am J Gastroenterol. 2000 March; 95 (3): 760-7, and Bergasa N V.; J Hepatol 2005 December; 43(6): 1078-88). Clinically, where a subjective and objective symptom on the basis of hepatic disorders, such as itching is observed, the PBC is called symptomatic PBC (sPBC), and where such a symptom is not observed, the PBC is called asymptomatic PBC (aPBC).

For the treatment of PBC, a fundamental treatment method has not been established, and symptomatic therapy is mainly employed. As the symptoms progresses, finally liver transplantation is performed. As a first-line drug for the treatment of PBC, ursodeoxycholic acid (UDCA) is widely used, however, in around 40% of patients, the effect of ursodeoxycholic acid does not sufficiently observed (Pares A, et al.; Gastroenterology. 2006; 130: 715-720). Recently (2016), obeticholic acid that is a farnesoid X receptor (FXR) agonist was approved in the United States as an agent for the treatment of PBC, however, there is a concern about safety, that is, the treatment with obeticholic acid, for example, increases the development of itching (Nevens F, et al.; N Engl J Med. 2016 Aug. 18; 375 (7): 631-43). In addition, it has been suggested from the results of multiple clinical trials that a fibrate drug (fenofibrate and bezafibrate) that is a peroxisome proliferator activated receptor (PPAR) a agonist used as an agent for the treatment of hyperlipidemia is useful for the treatment of PBC, however, the fibrate drug has not been approved as an agent for the treatment of PBC in any country (Iwasaki S, et al.; Hepatol Res. 1999; 16: 12-18, Hazzan R, et al.; J Clin Gastroenterol. 2010; 44: 371-373, Kurihara T, et al.; Am J Gastroenterol. 2002; 97: 212-214, Kurihara T, et al.; Am J Gastroenterol. 2000; 95: 2990-2992, Nakai S, et al.; Am J Gastroenterol. 2000; 95: 326-327, Ohmoto K, et al.; Liver. 2001; 21: 223-224, Takeuchi Y, et al.; J Gastroenterol Hepatol. 2011; 26: 1395-1401, Dohmen K, et al.; World J Gastroenterol. 2004; 10: 894-898, Han X F, et al.; J Dig Dis. 2012; 13: 219-224, Levy C, et al.; Aliment Pharmacol Ther. 2011; 33: 235-242, Liberopoulos E N, et al.; The Open Cardiovasc Med J. 2010; 4: 120-126, Ohira H, et al.; Am J Gastroenterol. 2002; 97: 2147-2149, and Hosonuma K, et al.; Am J Gastroenterol. 2015; 110: 423-431). As described above, until now, it cannot be said that an agent for the treatment of PBC is satisfactory present, and a novel therapeutic agent for the treatment of PBC, which is effective and safe, is desired.

In recent years, from the results of studies investigating the relationship between clinical outcomes (death or liver transplantation) and biomarkers for around 5000 patients with PBC, it has been reported that the decrease in levels of ALP and total bilirubin is strongly associated with the transplant-free survival time for patients with PBC, and it was revealed that the levels of ALP and total bilirubin are useful as the biomarkers for predicting the prognosis of PBC treatment (Lammers W J, et al.; Gastroenterology 2014; 147 (6): 1338-49. e1-e5). Accordingly, a compound that decreases the levels of ALP and total bilirubin is considered to be useful as an agent for the treatment of PBC.

Meanwhile, in WO 2005/023777, it has been disclosed that a compound represented by the following formula (1):

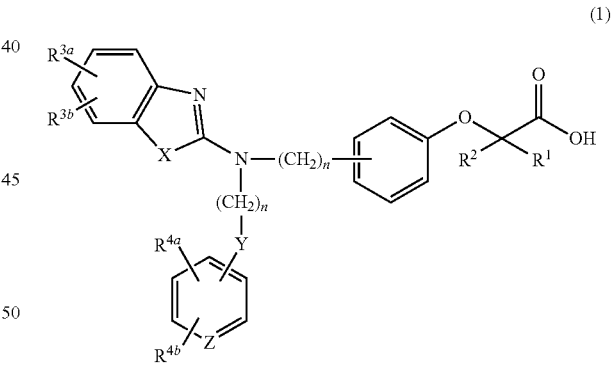

(in the formula, $R^1$ and $R^2$ are the same as or different from each other, and represent a hydrogen atom, a methyl group, or an ethyl group; $R^{3a}$, $R^{3b}$, $R^{4a}$, and $R^{4b}$ are the same as or different from one another, and represent a hydrogen atom, a halogen atom, a nitro group, a hydroxyl group, a $C_{1-4}$ alkyl group, a trifluoromethyl group, a $C_{1-4}$ alkoxy group, a $C_{1-4}$ alkylcarbonyloxy group, a di-$C_{1-4}$ alkyl amino group, a $C_{1-4}$ alkylsulfonyloxy group, a $C_{1-4}$ alkylsulfonyl group, a $C_{1-4}$ alkylsulfinyl group, or an $C_{1-4}$ alkylthio group, or $R^{3a}$ and $R^{3b}$ or $R^{4a}$ and $R^{4b}$ bind to each other and represent an alkylenedioxy group; X represents an oxygen atom, a sulfur atom, or N—$R^5$ ($R^5$ represents a hydrogen atom, a $C_{1-4}$ alkyl group, a $C_{1-4}$ alkylsulfonyl group, or a $C_{1-4}$ alkyloxycarbonyl group); Y represents an oxygen atom, a S(O)$_l$ group (l represents a number from 0 to 2), a carbonyl group, a carbonylamino group, an aminocarbonyl group, a sulfonylamino group, an aminosulfonyl group, or a NH group; Z represents CH or N; n represents a number from 1 to 6; m represents a number from 2 to 6), a salt thereof, or a solvate thereof has a selective PPAR α activation effect, and is useful as a prophylactic and/or therapeutic agent for, for example, hyperlipidemia, arteriosclerosis, diabetes, diabetic complication (for example, diabetic nephropathy), inflammation, or heart disease, which is not accompanied by weight gain or obesity in mammals including humans.

However, there is neither description nor suggestion as to how these compounds act on PBC.

SUMMARY

The present invention relates to provide a novel therapeutic agent for the treatment of PBC.

When conducted intensive studies, the present inventors have found that wholly unexpectedly, the compound disclosed as Example 85 in WO 2005/023777, that is, (R)-2-[3-[[N-(benzoxazol-2-yl)-N-3-(4-methoxyphenoxy)propyl]aminomethyl]phenoxy] butyric acid (hereinafter, may be referred to as "Compound A") decreases the levels of ALP and total bilirubin, and is useful for the treatment of PBC, and thus have completed the present invention.

That is, the present invention provides the following [1] to [12].

[1] A pharmaceutical composition for the treatment of primary biliary cirrhosis, containing a therapeutically effective amount of (R)-2-[3-[[N-(benzoxazol-2-yl)-N-3-(4-methoxyphenoxy)propyl]aminomethyl]phenoxy] butyric acid, a salt thereof, or a solvate thereof.
[2] The pharmaceutical composition described in [1], further containing a therapeutically effective amount of ursodeoxycholic acid.
[3] An agent for the treatment of primary biliary cirrhosis, containing (R)-2-[3-[[N-(benzoxazol-2-yl)-N-3-(4-methoxyphenoxy)propyl]aminomethyl]phenoxy] butyric acid, a salt thereof, or a solvate thereof as an active component.
[4] The agent for the treatment of primary biliary cirrhosis described in [3], further containing ursodeoxycholic acid as an active component.
[5] A method for the treatment of primary biliary cirrhosis, including administering (R)-2-[3-[[N-(benzoxazol-2-yl)-N-3-(4-methoxyphenoxy)propyl]aminomethyl]phenoxy] butyric acid, a salt thereof, or a solvate thereof to a patient in need thereof.
[6] The method for the treatment of primary biliary cirrhosis described in [5], further including administering ursodeoxycholic acid.
[7] Use of (R)-2-[3-[[N-(benzoxazol-2-yl)-N-3-(4-methoxyphenoxy)propyl]aminomethyl]phenoxy] butyric acid, a salt thereof, or a solvate thereof for the treatment of primary biliary cirrhosis.
[8] The use described in [7], in which ursodeoxycholic acid is combined.
[9] Use of (R)-2-[3-[[N-(benzoxazol-2-yl)-N-3-(4-methoxyphenoxy)propyl]aminomethyl]phenoxy] butyric acid, a salt thereof, or a solvate thereof for the production of a pharmaceutical composition for the treatment of primary biliary cirrhosis.
[10] Use of (R)-2-[3-[[N-(benzoxazol-2-yl)-N-3-(4-methoxyphenoxy)propyl]aminomethyl]phenoxy] butyric acid, a salt thereof, or a solvate thereof in combination with ursodeoxycholic acid for the production of a pharmaceutical composition for the treatment of primary biliary cirrhosis.

[11] An agent for reducing an alkaline phosphatase level, containing (R)-2-[3-[[N-(benzoxazol-2-yl)-N-3-(4-methoxyphenoxy)propyl]aminomethyl]phenoxy] butyric acid, a salt thereof, or a solvate thereof as an active component.
[12] An agent for reducing a total bilirubin level, containing (R)-2-[3-[[N-(benzoxazol-2-yl)-N-3-(4-methoxyphenoxy)propyl]aminomethyl]phenoxy] butyric acid, a salt thereof, or a solvate thereof as an active component.

The present invention is to provide a novel therapeutic agent that is useful for the treatment of PBC. In accordance with the present invention, a new option of the treatment for patients with PBC who cannot sufficiently obtain the effects by current therapeutic agents, and for patients with PBC who are difficult to use current therapeutic agents can be provided.

Figure 1:
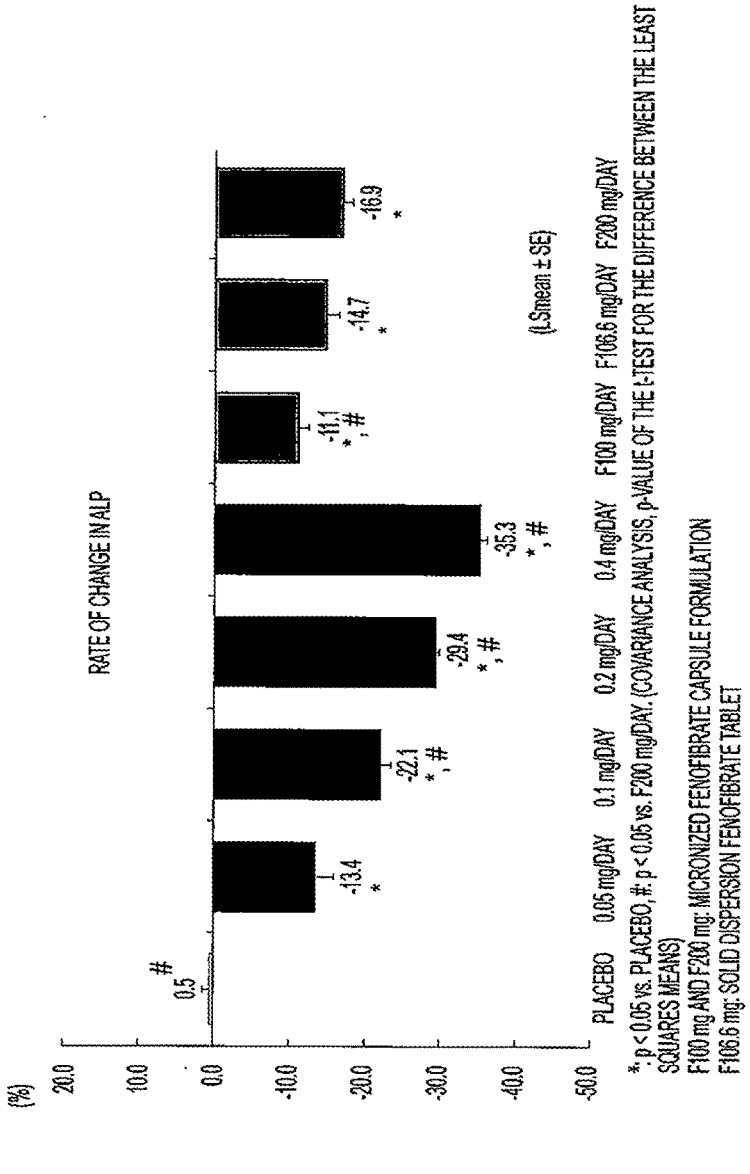
FIG. 1 illustrates the rate of change in ALP levels when Compound A (0.05 to 0.4 mg per day), fenofibrate (100 to 200 mg per day), or placebo is administered to patients with dyslipidemia showing a high level of triglyceride (TG)

DETAILED DESCRIPTION (R)-2-[3-[[N-(benzoxazol-2-yl)-N-3-(4-methoxyphenoxy)propyl]aminomethyl]phenoxy] butyric acid (Compound A) employed in the present invention is represented by the following formula (A):

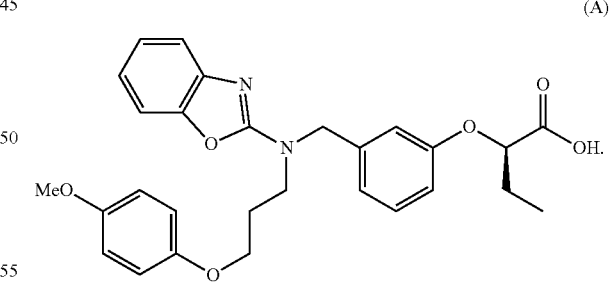

The compound can be produced in accordance with, for example, a method described in International Publication WO 2005/023777. Further, in accordance with the method described in a literature, the compound can also be formulated.

In addition, in one embodiment of the present invention, a salt or solvate of Compound A can also be used. A salt and a solvate can be produced by routine procedures. The salt of Compound A is not particularly limited as long as it is pharmaceutically acceptable, and for example, an alkali metal salt such as a sodium salt, and a potassium salt; an alkaline earth metal salt such as a calcium salt, and a magnesium salt; an organic base salt such as an ammonium salt, and a trialkyl amine salt; a mineral acid salt such as a hydrochloride, a sulfate; and an organic acid salt such as an acetate can be mentioned. As the solvate of Compound A or a salt thereof, a hydrate, and an alcohol solvate (for example, an ethanol solvate) can be mentioned.

In one embodiment of the present invention, by administering to a patient with PBC a pharmaceutical composition containing a therapeutically effective amount of Compound A, a salt thereof, or a solvate thereof, the PBC can be treated.

Regardless of the presence or absence of jaundice, the diagnosis of PBC is performed based on the following three items:
(1) cholestasis findings, that is, a level of ALP·γ-GTP being a biliary enzyme is increased;
(2) antimitochondrial antibody (AMA) positive findings (by an indirect immunofluorescence assay or an ELISA assay); and
(3) histological characteristic findings including chronic non-suppurative destructive cholangitis (CNSDC) (by liver biopsy). Liver biopsy is not essential in medical practice, and if the following items:
(1) abnormality of biliary enzyme (ALP·γ-GTP) is persistently observed;
(2) cholestasis caused by other causes of, for example, viruses, drugs, or alcohol is excluded;
(3) extrahepatic biliary obstruction is excluded by image inspection using ultrasound, CT, or MRI; and
(4) AMA is positive;
are satisfied, the patient can be diagnosed as PBC, however, in a case where AMA is negative, it is important that
(5) findings that are typical to or not contradictory to PBC are shown in liver biopsy. With reference to clinical practice guidelines in Japan, Europe, and the United States, basically, diagnosis of PBC can be made by findings of the ALP level increase and the AMA positive (see Clinical Practice Guidelines for Primary Biliary Cirrhosis (PBC), first edition, edited by a group of "Intractable Hepatobiliary Disease Study", Ministry of Health, Labour and Welfare, European Association for the Study of the Liver; Journal of Hepatology 51 (2009); 237-267, and Keith D. Lindor, et al.; HEPATOLOGY, Vol. 50, No. 1, 2009; 291-308).

In the present specification, unless otherwise indicated, the expression "PBC" means both symptomatic PBC (sPBC) having a subjective and objective symptom on the basis of hepatic disorders and asymptomatic PBC (aPBC) lacking such a symptom.

In the present specification, the term "treatment of PBC" refers to one or more selected from the group consisting of decreasing the levels of ALP and/or total bilirubin close to normal levels; relieving skin itching and/or fatigue, which are typical clinical symptoms of PBC; delaying or preventing the transition from asymptomatic PBC (aPBC) to symptomatic PBC (sPBC); and delaying or preventing the progression to liver cirrhosis or liver failure.

The levels of ALP and total bilirubin can be measured appropriately by those skilled in the art.

The normal level of ALP is assumed to be from 100 to 325 IU/L as measured by a Japan Society of Clinical Chemistry (JSCC) standardization correspondence method, and it is known that at the diagnosis of PBC, an abnormally high level is observed in around 80% of patients with PBC, and further, a level 3 times or more as high as the normal level may be shown in some cases. In one embodiment of the present invention, by administering Compound A, a salt thereof, or a solvate thereof to a patient with PBC, the blood concentration of ALP in the patient is decreased, and the PBC can be treated. In accordance with the present invention, in a patient with PBC, the level of ALP can be decreased to, for example, 2.5 times, 2 times, 1.8 times, 1.5 times, 1.2 times, 1.1 times, or 1.0 times or less as high as the normal level, and further, the level of ALP can be set to, but not limited to, for example, less than 1.67 times as high as the upper limit of the reference level of ALP. Alternatively, in a patient with PBC, the level of ALP can be decreased by, for example, 10%, 15%, 20%, 25%, 30%, 50%, or 75% from the level at the diagnosis of PBC.

In addition, in general, the normal level of total bilirubin is assumed to be from 0.2 to 1.2 mg/dL, and it is known that in a patient with PBC, the level of total bilirubin is increased due to the progress of cholestasis accompanying the disappearance of bile duct and the decrease in hepatocyte function. In one embodiment of the present invention, by administering Compound A, a salt thereof, or a solvate thereof to a patient with PBC, the increase in the blood concentration of total bilirubin in the patient is prevented, and the PBC can be treated. In accordance with the present invention, in a patient with PBC, the increase in the level of total bilirubin can be suppressed to, for example, 1.5 mg/dL, 1.75 mg/dL, 2.0 mg/dL, 2.5 mg/dL, 3.0 mg/dL, or 4.0 mg/dL or less. Alternatively, in a patient with PBC, the level of total bilirubin can be decreased by, for example, 10%, 15%, 20%, 25%, 30%, 50%, or 75% from the level before the administration.

In one embodiment of the present invention, by administering Compound A, a salt thereof, or a solvate thereof to a patient with PBC, the skin itching and/or fatigue can be relieved. The skin itching is a symptom that appears first in many patients with PBC, and as one of the causes, involvement of an increase in bile acid due to cholestasis is considered, however, the detailed cause is unknown. On the other hand, the fatigue symptom has not received much attention in Japan, however, is considered to be the most common symptom of PBC in Europe and the United States. In accordance with the present invention, the skin itching and/or fatigue can be relieved, therefore, the QOL of a patient with PBC can be improved. The skin itching and fatigue in a patient with PBC can be evaluated using PBC-27 or PBC-40 that is a disease-specific QOL rating scale.

It is known that some of the patients with asymptomatic PBC (aPBC) move to patients with symptomatic PBC (sPBC). Herein, aPBC and sPBC are classified according to the presence or absence of the subjective and objective symptom on the basis of hepatic disorders, and examples of the subjective and objective symptom include skin itching, jaundice, esophageal aneurysm, ascites, and hepatic encephalopathy. In one embodiment of the present invention, by administering Compound A, a salt thereof, or a solvate thereof to a patient with PBC, the transition from aPBC to sPBC can be delayed or prevented. That is, in accordance with the present invention, in a patients with PBC, the development of a subjective and objective symptom such as skin itching, jaundice, esophageal aneurysm, ascites, and hepatic encephalopathy can be delayed or suppressed.

As the PBC progresses, liver cirrhosis or liver failure is developed, and liver transplantation is performed as the final treatment. In one embodiment of the present invention, by administering Compound A, a salt thereof, or a solvate thereof to a patient with PBC, the liver function is improved, and the progression to liver cirrhosis or liver failure can be delayed or suppressed. Accordingly, in one embodiment of the present invention, by administering Compound A, a salt thereof, or a solvate thereof to a patient with PBC, the transplant-free survival time for the patient is prolonged, and the liver transplantation can be avoided.

In one embodiment of the present invention, Compound A, a salt thereof, or a solvate thereof may be used in combination with ursodeoxycholic acid that is the first-line drug for PBC. Specifically, to a UDCA-resistant patient with PBC who does not show improvement even when ursodeoxycholic acid (UDCA) is administered, Compound A, a salt thereof, or a solvate thereof can be administered in place of UDCA or in combination with UDCA. Where Compound A, a salt thereof, or a solvate thereof is used in combination with UDCA, Compound A, a salt thereof, or a solvate thereof, and UDCA may be administered singly alone, or simultaneously using a pharmaceutical composition containing both of the components to a patient with PBC. In a case of administering singly alone, either Compound A, a salt thereof, or a solvate thereof, or the UDCA may be administered first.

In one embodiment of the present invention, a pharmaceutical composition containing Compound A, a salt thereof, or a solvate thereof can be prepared in a dosage form of, for example, a tablet, a capsule, granules, powder, lotion, ointment, an injection, or a suppository by using other pharmaceutically acceptable carriers. These preparations can be produced by a known method.

In one embodiment of the present invention, Compound A, a salt thereof, or a solvate thereof can be administered by oral administration or parenteral administration, and preferably administered by oral administration. In addition, the therapeutically effective amount and the frequency of administration of Compound A, a salt thereof, or a solvate thereof vary depending on, for example, the body weight, age, sex, and symptom of a patient, however, can be appropriately set by those skilled in the art. For example, usually, in a case of an adult, as Compound A, 0.05 to 0.8 mg can be administered once or in 2 or 3 divided doses per day, preferably 0.2 to 0.4 mg is administered once or in 2 divided doses per day, and more preferably 0.1 to 0.8 mg is administered once or in 2 divided doses per day.

The contents of all patents and references explicitly cited in the present specification are incorporated herein in their entirety by reference. Further, the contents described in the specification and drawings of U.S. Patent Application No. 62/463,258 (filed Feb. 24, 2017) based on which the priority of the present application is claimed are incorporated herein in their entirety by reference.

EXAMPLES

Hereinafter, the present invention will be described in more detail by way of Examples, however, these Examples do not limit the present invention.

Example 1: Investigation of Effects of Compound A for ALP and Total Bilirubin

By using data (1965 cases in total) obtained in a clinical trial (8 tests with an administration period of 12 weeks or more) of Compound A, which had been performed for patients with dyslipidemia showing a high level of triglyceride (TG), the effects of Compound A for ALP and total bilirubin were investigated. Compound A was administered at a dose of 0.05 to 0.4 mg per day to Compound A group. Further, placebo or fenofibrate (100 to 200 mg per day) was administered to a control group. Each compound was administered to Compound A group and a control group for 12 weeks, and changes in the levels of ALP before and after the administration are shown in Table 1 and FIG. 1, and changes in the levels of total bilirubin before and after the administration are shown in Table 2 and FIG. 2. Note that comparisons between the groups were investigated by using covariance analysis with baseline levels used as covariates.

TABLE 1

Changes in ALP levels (IU/L)

| Group | n | Baseline | 12 Weeks | Rate of change (LSmean) | Standard error (SE) | P value* (vs. placebo) | P value* (vs. F200 mg) |
|---|---|---|---|---|---|---|---|
| Placebo | 298 | 234.2 | 233.3 | 0.5 | 0.8 | — | <.0001 |
| 0.05 mg/day | 37 | 234.4 | 201.5 | −13.4 | 2.4 | <.0001 | 0.1922 |
| 0.1 mg/day | 127 | 228.4 | 177.4 | −22.1 | 1.3 | <.0001 | 0.0041 |
| 0.2 mg/day | 846 | 235.6 | 164.7 | −29.4 | 0.5 | <.0001 | <.0001 |
| 0.4 mg/day | 319 | 225.1 | 145.0 | −35.3 | 0.8 | <.0001 | <.0001 |
| F100 mg/day | 122 | 226.3 | 198.7 | −11.1 | 1.3 | <.0001 | 0.0012 |
| F106.6 mg/day | 76 | 235.3 | 198.8 | −14.7 | 1.7 | <.0001 | 0.2866 |
| F200 mg/day | 140 | 222.5 | 182.5 | −16.9 | 1.2 | <.0001 | — |

*Covariance analysis, p-value of the t-test for the difference between the least squares means
F100 mg and F200 mg: micronized fenofibrate capsule formulation
F106.6 mg: solid dispersion fenofibrate tablet

TABLE 2

Changes in total bilirubin levels (mg/dL)

| Group | n | Baseline | 12 Weeks | Rate of change (LSmean) | Standard error (SE) | P value* (vs. placebo) | P value* (vs. F200 mg) |
|---|---|---|---|---|---|---|---|
| Placebo | 298 | 0.8 | 0.8 | 6.1 | 1.5 | — | <.0001 |
| 0.05 mg/day | 37 | 0.8 | 0.6 | −16.4 | 4.3 | <.0001 | 0.1412 |
| 0.1 mg/day | 127 | 0.8 | 0.7 | −7.7 | 2.3 | <.0001 | 0.6181 |
| 0.2 mg/day | 846 | 0.8 | 0.7 | −11.9 | 0.9 | <.0001 | 0.2817 |
| 0.4 mg/day | 319 | 0.8 | 0.6 | −10.4 | 1.5 | <.0001 | 0.6851 |
| F100 mg/day | 122 | 0.8 | 0.7 | −5.2 | 2.4 | <.0001 | 0.2003 |
| F106.6 mg/day | 76 | 0.8 | 0.7 | −4.2 | 3.0 | 0.0023 | 0.1722 |
| F200 mg/day | 140 | 0.9 | 0.7 | −9.3 | 2.2 | <.0001 | — |

Figure 2:
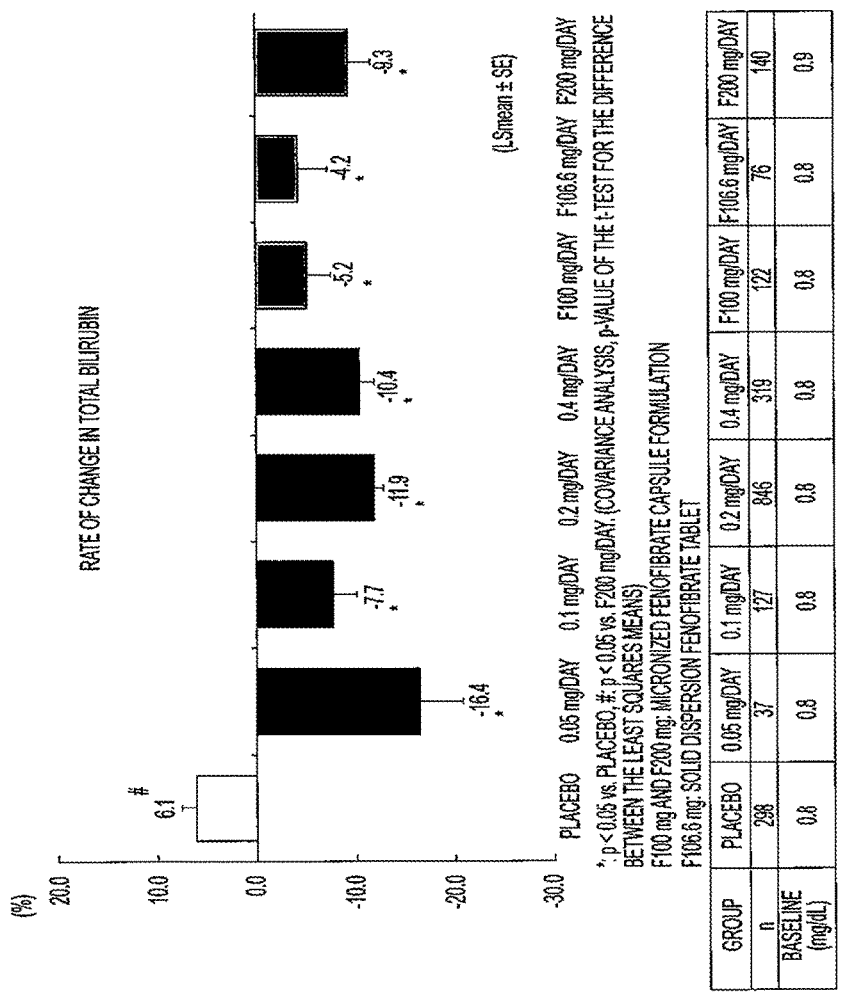
FIG. 2 illustrates the rate of change in total bilirubin levels when Compound A (0.05 to 0.4 mg per day), fenofibrate (100 to 200 mg per day), or placebo is administered to patients with dyslipidemia showing a high level of triglyceride (TG)

*Covariance analysis, p-value of the t-test for the difference between the least squares means
F100 mg and F200 mg: micronized fenofibrate capsule formulation
F106.6 mg: solid dispersion fenofibrate tablet As shown in Tables 1 and 2 and FIGS. 1 and 2, it was confirmed that Compound A decreases dose-dependently the levels of ALP and total bilirubin as compared with placebo. Further, when Compound A group was compared with the control group to which fenofibrate being suggested to be useful for the treatment of PBC had been administered, it was revealed that Compound A at a dose of 0.1 mg or more decreases the level of ALP more strongly than the fenofibrate at the maximum clinical dose (200 mg per day). Therefore, it was found that Compound A is useful as an agent for the treatment of PBC.

Example 2: Investigation of Effects of Compound A for ALP and Total Bilirubin in Patients being Treated with Ursodeoxycholic Acid Data of patients being treated with ursodeoxycholic acid (15 cases in total) were extracted from the data obtained in a clinical trial (8 tests with an administration period of 12 weeks or more) of Compound A, which had been performed for patients with dyslipidemia showing a high level of TG, the effects of Compound A for the ALP and the total bilirubin were investigated. Compound A was administered at a dose of 0.05 to 0.4 mg per day to Compound A group. Further, placebo was administered to a control group. Each compound was administered to Compound A group and a control group for 12 weeks, and changes in the levels of ALP before and after the administration are shown in Table 3 and FIG. 3, and changes in the levels of total bilirubin before and after the administration are shown in Table 4 and FIG. 4. Note that comparisons between the groups were investigated by using covariance analysis with baseline levels used as covariates.

Figure 3:
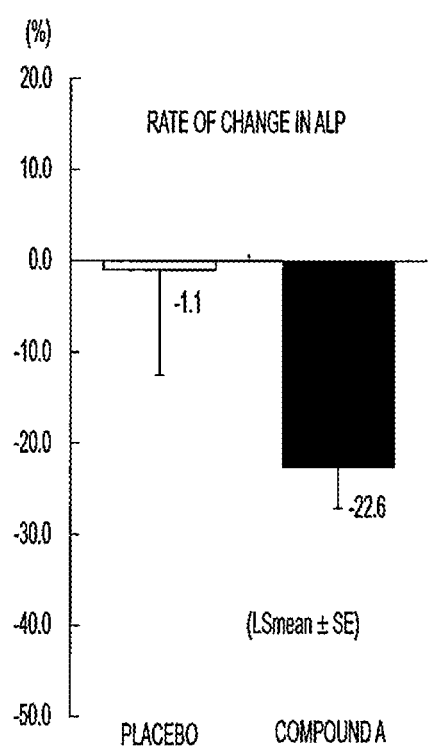
FIG. 3 illustrates the rate of change in ALP levels when Compound A (0.05 to 0.4 mg per day) or placebo is administered to patients with dyslipidemia showing a high level of TG and during treatment with UDCA.
Figure 4:
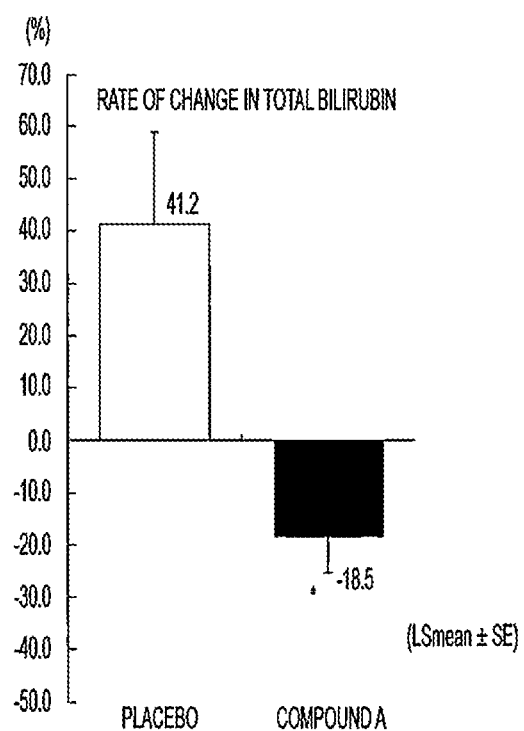
FIG. 4 illustrates the rate of change in total bilirubin levels when Compound A (0.05 to 0.4 mg per day) or placebo is administered to patients with dyslipidemia showing a high level of TG and during treatment with UDCA.

As shown in Tables 3 and 4 and FIGS. 3 and 4, in patients being treated with ursodeoxycholic acid, it was revealed that Compound A decreases the levels of ALP and total bilirubin. Therefore, it was found that Compound A is useful as an agent for the treatment of PBC, also for the patient being treated with ursodeoxycholic acid.

As described above, from Examples 1 and 2, Compound A of the present invention decreases the levels of both ALP and total bilirubin, which are biomarkers for predicting the prognosis of treatment of PBC, therefore, it was revealed that Compound A of the present invention is highly useful as an agent for the treatment of PBC.

INDUSTRIAL APPLICABILITY

The present invention was completed on the basis of the finding that Compound A has an effect of decreasing the levels of ALP and total bilirubin for the first time, and is useful as a medicine for the treatment of PBC.

What is claimed is:

1. A method for the treatment of primary biliary cirrhosis, comprising administering (R)-2-[3-[[N-(benzoxazole-2-yl)-N-3-(4-methoxyphenoxy)propyl]aminomethyl]phenoxy] butyric acid, a salt thereof, or a solvate thereof to a patient in need thereof.

2. The method for the treatment of primary biliary cirrhosis according to claim 1, further comprising administering ursodeoxycholic acid.

3. The method for the treatment of primary biliary cirrhosis according to claim 1, wherein the (R)-2-[3-[[N-(benzoxazole-2-yl)-N-3-(4-methoxyphenoxy)propyl]aminomethyl]phenoxy] butyric acid, a salt thereof, or a solvate thereof is administered to the patient in a daily dose of 0.05 to 0.8 mg.

TABLE 3

Changes in ALP levels (IU/L)

| Group | n | Baseline | 12 Weeks | Rate of change (LSmean) | Standard error (SE) | P value* (vs. placebo) |
|---|---|---|---|---|---|---|
| Placebo | 2 | 320.5 | 322.0 | −1.1 | 11.5 | — |
| Compound A | 13 | 295.5 | 229.5 | −22.6 | 4.5 | 0.1064 |

*Covariance analysis, p-value of the t-test for the difference between the least squares means

TABLE 4

Changes in total bilirubin levels (mg/dL)

| Group | n | Baseline | 12 Weeks | Rate of change (LSmean) | Standard error (SE) | P value* (vs. placebo) |
|---|---|---|---|---|---|---|
| Placebo | 2 | 0.6 | 0.9 | 41.2 | 17.8 | — |
| Compound A | 13 | 0.7 | 0.6 | −18.5 | 6.9 | 0.0089 |

*Covariance analysis, p-value of the t-test for the difference between the least squares means 4. The method for the treatment of primary biliary cirrhosis according to claim 1, wherein the administering decreases the level of total bilirubin in the patient.

5. The method for the treatment of primary biliary cirrhosis according to claim 4, wherein the decrease in the level of total bilirubin in the patient is a decrease of 10% to 75% compared to the level before administration.

* * * * *